(12) United States Patent
Hoskins

(10) Patent No.: US 10,676,453 B1
(45) Date of Patent: Jun. 9, 2020

(54) DECARBOXYLATION PROCESS

(71) Applicant: Alan Hoskins, Silver Springs, NV (US)

(72) Inventor: Alan Hoskins, Silver Springs, NV (US)

( * ) Notice: Subject to any disclaimer, the term of this patent is extended or adjusted under 35 U.S.C. 154(b) by 0 days.

(21) Appl. No.: 16/358,997

(22) Filed: Mar. 20, 2019

(51) Int. Cl.
*C07D 311/80* (2006.01)

(52) U.S. Cl.
CPC .................. *C07D 311/80* (2013.01)

(58) Field of Classification Search
CPC ..................................... C07D 311/80
USPC ........................................ 549/390
See application file for complete search history.

(56) References Cited

U.S. PATENT DOCUMENTS

| | | |
|---|---|---|
| 7,700,368 B2 | 4/2010 | Flockhart et al. |
| 2006/0167283 A1 | 7/2006 | Flockhart et al. |

OTHER PUBLICATIONS

Gallily, Ruth et al., The Anti-Inflammatory Properties of Terpenoids from Cannabis, Cannabis and Cannabinoid Research, vol. 2.1, 2018, pp. 282-290, Mary Ann Liebert, Inc., Publishers, New Rochelle NY.
Russo, Ethan B, Taming THC: potential cannabis synergy and phytocannabinoid-terpenoid entourage effects, British Journal of Pharmacology 163, 2011, pp. 1344-1364.

*Primary Examiner* — Taylor V Oh
(74) *Attorney, Agent, or Firm* — Stefan J. Kirchanski; Matthew J. Spark; Zuber Lawler & Del Duca LLP

(57) ABSTRACT

A process to decarboxylate THCA in *cannabis* material while minimizing the thermal decomposition of THC and the loss of volatile components such as terpenoids consists of four steps. Prepared *cannabis* material is first heated to about 105° C. for 20 min. to complete the dehydration of the material. The processing temperature is then increased to about 110° C. for about 30 min. to start the decarboxylation process. Thereafter, the temperature is increased to about 115° C. for about 35 min. Finally, the temperature is increased by about 2.5° C. (but not exceeding 118° C.) for about an additional 15 min. to complete the decarboxylation.

1 Claim, No Drawings

DECARBOXYLATION PROCESS

CROSS-REFERENCE TO PRIOR APPLICATIONS

Not applicable.

U.S. GOVERNMENT SUPPORT

Not applicable.

BACKGROUND OF THE INVENTION

Area of the Art

The invention is in the area of natural plant products and is more specifically directed to an improved process for decarboxylation of cannabinoids in plant material.

Description of the Background Art

Worldwide *cannabis* (*Cannabis sativa* L.) is becoming increasingly important both as a medicinal and recreational herbal product. Like many green land plants (GLP) *cannabis* plant material contains a variety of secondary metabolites (called "natural products") that give the plant material a characteristic odor and taste. Many spices and natural flavors are such secondary metabolites of GLPs. Many important medicinal molecules are also GLP secondary metabolites or are derived from such metabolites. GLPs expend a great amount of energy synthesizing an incredibly wide variety of such metabolites, and it has long been theorized that these molecules serve a beneficial role for the plants such as protecting the plants from insect (or other predators) or from various bacterial and fungal diseases or luring animals into performing important tasks such as pollinating flowers. Unfortunately, for the plants at least, many plant predators, including human beings, have actually developed a taste for the various plant-based natural products.

Natural products show a variety of physiological or "drug" effects when ingested. Presumably, this biological activity evolved as part of the "protective" role of natural products. A surprisingly large number of natural products show central nervous system activity. For example, the opium poppy (*Papaver somnifera*) produces morphine and other opiates, which interact with opiate receptors in the central nervous system of animals. The opiate receptors do not exist to interact with morphine; rather the opiate receptors interact with naturally existing neural transmitters, and the opium poppy has evolved a molecule to co-opt the natural neural transmitters—presumably to disrupt the neural functioning of predating insects. Humans have discovered that opiates can modulate the nervous system in positive ways (e.g., sleep and pain relief). As a result, a tremendous quantity of opiates are used each year as legal and illegal drugs.

Similarly, the *cannabis* plant produces a series of cannabinoid molecules that interact with one or more cannabinoid receptors in the central nervous system. The precise function of the cannabinoid receptors is still a matter of research, but various cannabinoid molecules show a number of central nervous system as well as immunological effects. Tetrahydrocannabinol (THC) show significant central nervous system effects, and THC is primarily responsible for the psychoactive aspects of *cannabis* ingestion. On the other hand, a major cannabinoid, cannabidiol (CBD) does not show psychoactive effects but does show major anti-inflammatory effects.

Medical and recreational *cannabis* are legal in an ever-increasing number of States and foreign countries. When *cannabis* was totally a black market product, little attention was paid to health and safety or to quality control of the end product. *Cannabis* material was often contaminated with pesticides and mold picked up when the plant material was dried and aged. Although different cultivars ('strains' in the *cannabis* world) can have dramatically different chemical profiles differing significantly in amounts and types of cannabinoids as well as in amounts and types of other significant natural products such as terpenes and terpenoids, improper storage or processing often obscured these differences. Now, much greater care is taken in the storage and processing of *cannabis* material to avoid contamination and to preserve the natural chemical profile ('chemo-type') of the source *cannabis* material. As might be expected THC is usually considered the most important constituent of *cannabis* materials.

The increased care and quality control of *cannabis* products has brought to light something that was well known by natural product chemists but not by all *cannabis* aficionados—namely *cannabis* plants do not directly synthesize any THC. Rather the plant synthesizes Tetrahydrocannabinolic acid (THCA), and this cannabinoid is without any psychoactive properties. However, THCA may spontaneously decarboxylate during the drying process if the drying temperature is sufficiently high. In addition, when *cannabis* material is burned, significant decarboxylation occurs so that the resulting smoke contains significant quantities of THC and little, if any, THCA. However, large amounts of *cannabis* is now used as an ingredient in edible products and unless the processing (e.g., baking *cannabis* cakes) provides adequate decarboxylation conditions, the effectiveness of the edibles may vary significant from batch to batch. While it is possible to dry and process the raw *cannabis* plant material at high temperatures to ensure total or near total decarboxylation, such processing removes significant quantities of terpenoids and other volatile molecules. This changes the taste as well as the effectiveness of the resulting material. Thus, THCA to THC decarboxylation poses a problem in that improper processing (either too hot or too cold) negatively effects the end product. What is needed is a reliable way of achieving near complete decarboxylation while causing minimal changes in the amounts of other cannabinoids and volatile *cannabis* constituents.

Published U.S. Patent Application No. 2006/0167283 suggests a temperature profile for decarboxylation of CBDA. The reference suggests starting at 100-110° C. (preferably 105° C.) for 15 min to remove moisture. Then, the temperature is raised to 115 C to 125° C. for 45-75 min (typically 120° C. for 60 min) or (more preferably) 135° C.-145° C. for 15-45 min. U.S. Pat. No. 7,700,368 recites a similar decarboxylation process. This reference proposes a two-step process with the first step being a short step (10-20 min) at 100-110° C. This is followed by a second of 115-125° C. for 45-75 min or 135-145° C. for 15-45 min.

SUMMARY OF THE INVENTION

The present invention provides an effective way to decarboxylate THCA in *cannabis* material while minimizing the thermal decomposition of THC and the loss of volatile components such as terpenoids. The preferred process is a four step process where the initial step is to heat the prepared cannabis material to about 105° C. for 20 min. to complete the dehydration of the material. The processing temperature is then increased to about 110° C. for about 30 min. to start the decarboxylation process. Thereafter, the temperature is increased to about 115° C. for about 35 min. Finally, the temperature is increased by about 2.5° C. (not exceeding 118° C.) for about an additional 15 min. to complete the decarboxylation. This process results in complete decarboxylation with decreased (as compared to prior art processes) decomposition of THC. In addition, the inventive four-step process spares more of the volatile terpenoids that does the prior art process.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an improved decarboxylation process for *cannabis* material.

As discussed above, THCA spontaneously decarboxylates to THC at temperatures significantly above 100° C. although at 100° C. the conversion is extremely slow. The preferred decarboxylation temperatures are in the range of 120° C. to 145° C. Elevating the decarboxylation temperature increases the rate of decarboxylation, but at temperatures of 125° C. and higher there may be considerable breakdown of THC into Cannabinol (CBN) which is not psychoactive. Also, one would expect higher temperatures to increase the loss of volatile constituents such as the terpenoid components.

Because it is believed that the terpenoids may affect the physiological effects of *cannabis* ingestion (the so-called "entourage" effect) and because the volatile components give each cultivar ("strain") of *cannabis* its distinct organoleptic properties, sophisticated consumers tend to reject *cannabis* products in which the amount and/or proportions of the various volatile components have been significantly altered.

Perhaps an example based on artisanal coffees might serve here. Essentially, people consume coffee for two reasons: they like the physiological effects of caffeine (it makes you alert), and they like the flavor of the coffee beverage. Virtually all varieties of coffee have plentiful caffeine although fermentation and bean processing can change the amount of caffeine in the final product. So why do people pay premium prices for artisanally roasted coffee varieties? Because not only do these varietal coffees provide caffeine, they also have distinct tastes and odors. Incorrect processing will destroy the distinctive qualities of premium coffee varieties.

Similarly, *cannabis* has a relatively limited number of "active" ingredients. The main psychotropic effect is provided by THC although other cannabinoids may have an influence. The various volatile terpenoids may contribute to the psychoactive effect and are primarily responsible for taste and smell of the product. Insufficient decarboxylation lowers the psychotropic effect while excess heating alters the organoleptic properties of premium *cannabis* cultivars and also may decrease the psychotropic effects by destroying THC.

The present invention offers optimal decarboxylation of *cannabis* "flower" material while preserving the desirable organoleptic properties of the volatile components. Traditionally, little attention was paid to decarboxylation. *Cannabis* material was "cured" at a somewhat elevated temperature to dehydrate the plant material before molds or other decomposing microorganisms had a chance to take over. During the "curing" a reasonably high degree of decarboxylation took place although volatile constituents were often lost at the same time. Today a much more controlled "curing" is undertaken. Most common is what I shall call the two-step process in which the *cannabis* material is first heated to a relatively low temperature (95-110° C.) to drive off any residual water. Then, the material is heated to a higher temperature (usually 125° C. or higher) to decarboxylate the THCA. I have discovered that it is preferable to raise the temperature in a number of stages to a maximum temperature of about 118° C. even though the prior art indicates that decarboxylation below 120° C. is generally believed to be excessively slow.

My process uses four steps as indicated in Table 1. The data reported here were produced using an electric oven having the typical consumer oven dimensions of about 64 cm. (25 in) wide by 41 cm. (16 in). deep and 41 cm (16 in.) high. Batches of *cannabis* material weighing about 1.8 kg (4 lb.) were treated. The *cannabis* material was *cannabis* "flower" or "bud" material (largely floral bracts) that had been chopped into fine "flour-like" fragments generally about 0.1 mm by 0.1 mm or fine (a commercial herb grinder-mill such as those produced by Schutte Hammermill of Buffalo, N.Y. are suitable). The *cannabis* material was evenly divided into three 4.73 L (5 qt.) glass dishes with dimensions of about 43 cm. (17 in.) long by 28 cm. (11 in.) wide and 6.3 cm. (2.5 in) high. Each dish contained a layer of *cannabis* material about 2.54 cm. (1 in.) thick. The dishes were sealed with a layer of aluminum foil.

First, the oven is heated to about 105° C.±1° C. for about 20 min. to drive off residual water. Next the oven temperature is increased by 5±1° C. and the material is allowed to "bake" for about 30 min. It will be appreciated that simply raising the oven temperature does not instantly increase the internal temperature of the *cannabis* material. However, because the *cannabis* material is spread out in a relatively thin layer, all of the material reaches the new temperature within a few minutes at most. After 30 min, the oven temperature is raised by an additional 5-±1° C. for an additional 35 min of "cooking." Finally, the temperature is raised by 2.5±1° C. for an additional 15 min. Significantly, the maximum temperature does not exceed about 118° C. which is somewhat lower than the temperature recommended by the prior art (at least 120° C., but preferably 135° C.-145° C.).

TABLE 1

Inventive Four Step Process

| Step | Duration |
| --- | --- |
| 1) Preheat, dehydrate at 105° C. ± 1° C. | 20 min. |
| 2) Increase heat by 5 ± 1° C. | 30 min |
| 3) Increase heat by 5 ± 1° C. | 35 mm |
| 4) Increase heat by 2.5 ± 1° C., but not above about 118° C. | 15 min |

The inventive process was compared to a two-step process (Table 2) that is representative of a typical of the prior art process. Amounts of *cannabis* material and oven arrangement were the same as with the inventive process. *Cannabis* material was heated to 105° C.±1° C. for 20 min. to drive off moisture. Then the temperature was raised to 125-±1° C. for 80 min for decarboxylation. The amounts of *cannabis* material and oven configuration were identical for the inventive process and for the prior art "two-step" process.

TABLE 2

Prior Art Two Step Process

| Step | Duration |
|---|---|
| 1) Preheat, dehydrate at 105° C. ± 1° C. | 20 min. |
| 2) Decarboxylate at 125 ± 1° C. | 80 min |

Table 3 shows the cannabinoid analysis (by UV HPLC) of the starting "*cannabis*" "flower" material that was used in all the tests. Note that the starting material contains 19.80% by weight total cannabinoids. The vast majority of the cannabinoids is present as THCA although there is 1.16% by weight $\Delta^9$-THC. There is also a small amount of CBGA. This should be contrasted with Table 4 that shows the cannabinoid level present after treatment of the starting material with the inventive four-step process. The total amount of cannabinoids is almost identical (19.54% by weight as opposed to 19.80% by weight for the starting material). However, in this case there is 18.31% by weight $\Delta^9$-THC and no THCA. As desired, the process resulted in complete decarboxylation of the THCA. In addition, the CBGA in the starting material was all decarboxylated into CBG. There is also a small amount of CBN (0.344% by weight) which was not present in the starting material. CBN is known to be a breakdown product of $\Delta^9$-THC so it is likely that a very small amount of THC decomposition has taken place. The analysis also shows 0.224% by weight CBC. However, it is believed that this is likely an artifact because the LOD (limit of detection) for CBC is 0.6% by weight. Therefore, the level detected for CBC may well be incorrect. These results should be contrasted with the results for the prior art two-step process (Table 5). Here the total cannabinoid level is 16.55% by weight so there has been an approximately 3% loss in total cannabinoids. THCA has been all decarboxylated, but only 15.22% by weight $\Delta^9$-THC is detected. It seems likely that the "missing" cannabinoids are a result of thermal decomposition of the THC. The prior art process produces 0.74% by weight (twice as much as the inventive process) CBN—a known decomposition product of THC. These results are unexpected because the prior art process uses a decarboxylation temperature at the very low end of that commonly used which suggests that many prior art decarboxylation schemes actually destroy significant amounts of THC.

TABLE 3

Cannabinoids in Starting Material

| Analyte | Amount Detected (% w/w) |
|---|---|
| CBC (Cannabichromene) | None detected |
| CBCA (Cannabichromene acid) | None detected |
| CBD | None detected |
| CBDA (Cannabidiol acid) | None detected |
| CBG (Cannabigerol) | None detected |
| CBGA (Cannabigerol acid) | 0.665% |
| CBN | None detected |
| $\Delta^8$-THC | None detected |
| $\Delta^9$-THC | 1.160% |
| THCA | 17.980% |
| Total cannabinoids | 19.805% |

TABLE 4

Cannabinoids after Inventive Process

| Analyte | Amount Detected (% w/w) |
|---|---|
| CBC | 0.224%* |
| CBCA | None detected |
| CBD | None detected |
| CBDA | None detected |
| CBG | 0.661% |
| CBGA | None detected |
| CBN | 0.334% |
| $\Delta^8$-THC | None detected |
| $\Delta^9$-THC | 18.311% |
| THCA | None detected |
| Total cannabinoids | 19.54% |

* Below the LOD.

TABLE 5

Cannabinoids after Prior Art Two Step Process

| Analyte | Amount Detected (% w/w) |
|---|---|
| CBC | None detected |
| CBCA | None detected |
| CBD | None detected |
| CBDA | None detected |
| CBG | 0.599% |
| CBGA | None detected |
| CBN | 0.738% |
| $\Delta^8$-THC | None detected |
| $\Delta^9$-THC | 15.215% |
| THCA | None detected |
| Total cannabinoids | 16.552% |

Besides the physiologically active cannabinoids, the terpene and terpene-like (terpenoid) molecules are important for the overall quality of a *cannabis* product. While it is quite possible that the terpenoids interact with the cannabinoids and alter the overall physiological effect of the product, it is incontrovertible that the terpenoids contribute significantly to the organoleptic properties of the product. As is the case with fine coffee or wine, the users key in on the taste and smell of the product, and it becomes an important part of the enjoyment of the product. As a whole, terpenoids are volatile, and it is not unexpected to lose terpenoids during processing. In the inventive process, the foil cover over the *cannabis* is intended to impede loss of volatiles. If all of the terpenoids are lost or greatly reduced in level, a user will find the product to taste "dead" or stale. Because different terpenoids have very different tastes and smells, if processing strongly shifts the balance of terpenoid species, the overall character of the product will be changed. As shown in Table 6, the starting material contained 0.84% by weight total terpenoids as determined by head space gas chromatography using a flame ionization detector (HS-GC/FID). Ten different terpenoids were detected with the major species (more than 0.1% by weight) species being D-Limonene, Linalool and β-Caryophyllene. The Caryophyllene is believed to be responsible for the distinctive *cannabis* odor that some find unpleasant. As would be expected, the heated decarboxylation step results in a loss of volatile terpenoids. The inventive process shows (Table 7) a reduction in total terpenoids to 0.35% by weight terpenoids spread across eight different terpenoid species (Camphene and α-Pinene are lost or reduced to undetectable levels) with Linalool (0.12% by weight) and β-Caryophyllene (0.139% by weight) being the major species. The prior art process (Table 8) causes even more terpenoid loss showing a total terpenoid level of 0.26% spread across seven species (Camphene, α-Pinene and β-Myrcene are lost or reduced to undetectable levels). The only terpenoid remaining above 0.1% is β-Caryophyllene (0.111% by weight). The inventive process preserves a greater range of terpenoids as well as the relationships between the various terpenoids than does the prior art process.

TABLE 6

Terpenoids in Starting Material

| Analyte | Amount Detected (% w/w) |
| --- | --- |
| Camphene | 0.006% |
| Linalool | 0.189% |
| α-Bisabolol | 0.011% |
| α-Humulene | 0.043% |
| α-Pinene | 0.018% |
| β-Caryophyllene | 0.149% |
| β-Myrcene | 0.037% |
| β-Pinene | 0.069% |
| D-Limonene | 0.305% |
| Trans-Nerolidol | 0.008% |
| Total terpenoids | 0.84% |

TABLE 7

Terpenoids after Inventive Process

| Analyte | Amount Detected (% w/w) |
| --- | --- |
| Camphene | None detected |
| Linalool | 0.120% |
| α-Bisabolol | 0.013% |
| α-Humulene | 0.043% |
| α-Pinene | None detected |
| β-Caryophyllene | 0.139% |
| β-Myrcene | 0.004% |
| β-Pinene | 0.002% |
| D-Limonene | 0.024% |
| Trans-Nerolidol | 0.009% |
| Total terpenoids | 0.35% |

TABLE 8

Terpenoids after Prior Art Process

| Analyte | Amount Detected (% w/w) |
| --- | --- |
| Camphene | None detected |
| Linalool | 0.073% |
| α-Bisabolol | 0.011% |
| α-Humulene | 0.037% |
| α-Pinene | None detected |
| β-Caryophyllene | 0.111% |
| β-Myrcene | None detected |
| β-Pinene | 0.002% |
| D-Limonene | 0.015% |
| Trans-Nerolidol | 0.008% |
| Total terpenoids | 0.26% |

While the data presented here are produced using a small test oven, the inventive process has also been verified in larger commercial ovens. With an oven, having a height of about 145 cm with a width of about 965 cm and depth of 940 cm batches of about 5 kg arranged in glass dishes as explained above can be accommodated. When the thickness of the *cannabis* material is the same as that used in the test oven, the results are substantially the same as the test results presented here. The commercial oven is equipped with convection oven features. Surprisingly, the use of convection heating does not appreciably speed up the process. It is believed that because *cannabis* material is sealed with foil, moving hot air (convection) does not increase the rate at which the temperature of the *cannabis* material increases. The process can be scaled to ovens of virtually any size.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just described preferred embodiment could be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. An improved method for decarboxylation of *cannabis* plant material while limiting loss of terpenoids and thermal decomposition of tetrahydrocannabinol consisting essentially of the steps of:
   heating an aliquot of *cannabis* plant material to a temperature of 105° C.±1° C. for about 20 minutes;
   increasing temperature by 5±1° C. for about 30 minutes;
   raising temperature by 5±1° C. for about 35 minutes; and
   elevating temperature by 2.5±1° C. for about 15 minutes, wherein temperature does not exceed about 118° C. whereby the *cannabis* plant material is decarboxylated while limiting the loss of terpenoids and thermal decomposition of tetrahydrocannabinol.

* * * * *